US009566240B2

(12) United States Patent
Burch et al.

(10) Patent No.: US 9,566,240 B2
(45) Date of Patent: Feb. 14, 2017

(54) COMPOSITIONS FOR MULTIPHASE, STAGGERED, OR SUSTAINED RELEASE OF AN ACTIVE SUBSTANCE

(71) Applicant: CLABBER GIRL CORPORATION, Terre Haute, IN (US)

(72) Inventors: Joseph J. Burch, West Terre Haute, IN (US); Patrick A. Jobe, Becker, MN (US)

(73) Assignee: CLABBER GIRL CORPORATION, Terre Haute, IN (US)

( * ) Notice: Subject to any disclaimer, the term of this patent is extended or adjusted under 35 U.S.C. 154(b) by 0 days.

(21) Appl. No.: 14/735,507

(22) Filed: Jun. 10, 2015

(65) Prior Publication Data

US 2016/0106675 A1  Apr. 21, 2016

Related U.S. Application Data

(60) Provisional application No. 62/064,140, filed on Oct. 15, 2014.

(51) Int. Cl.
| | | |
|---|---|---|
| *A61K 9/50* | (2006.01) | |
| *A61K 9/16* | (2006.01) | |
| *A61K 9/20* | (2006.01) | |
| *A61K 33/00* | (2006.01) | |

(52) U.S. Cl.
CPC ............... *A61K 9/16* (2013.01); *A23K 20/22* (2016.05); *A23K 40/35* (2016.05); *A61K 9/1617* (2013.01); *A61K 9/1623* (2013.01); *A61K 9/1635* (2013.01); *A61K 9/1652* (2013.01); *A61K 9/1658* (2013.01); *A61K 9/2081* (2013.01); *A61K 9/5047* (2013.01); *A61K 33/00* (2013.01); *A23K 50/10* (2016.05)

(58) Field of Classification Search
CPC ............................ A61K 9/5047; A61K 9/2081
See application file for complete search history.

(56) References Cited

U.S. PATENT DOCUMENTS 3,247,066 A   4/1966  Milosovich, Jr.

FOREIGN PATENT DOCUMENTS

| EP | 0 132 245 A2 | 1/1985 |
|---|---|---|
| WO | 98/07324 A1 | 2/1998 |
| WO | 98/38869 A1 | 9/1998 |

OTHER PUBLICATIONS

Jan. 18, 2016 International Search Report issued in International Application No. PCT/US2015/055514.
Jan. 18, 2016 Written Opinion of the International Searching Authority issued in International Application No. PCT/US2015/055514.
Choudhari et al., "Extended Release Dosage Forms—Novel Drug Delivery System," International Journal for Pharmaceutical Research Scholars (IJPRS), vol. 3, No. 2, pp. 717-728, Jun. 22, 2014.

*Primary Examiner* — Carlos Azpuru
(74) *Attorney, Agent, or Firm* — Oliff PLC

(57) ABSTRACT

A composition having a mixture of discreet particles, each particle comprising an active substance and a coating material, the active substance being at least partially coated with the coating material. The mixture of discreet particles includes a first batch of first particles, the first particles of the first batch having a first average weight % ratio of the active substance to the coating material; and a second batch of second particles, the second particles of the second batch having a second average weight % ratio of the active substance to the coating material, the second average weight ratio being different from the first average weight ratio.

11 Claims, 12 Drawing Sheets

COMPOSITIONS FOR MULTIPHASE, STAGGERED, OR SUSTAINED RELEASE OF AN ACTIVE SUBSTANCE

This nonprovisional application claims the benefit of U.S. Provisional Application No. 62/064,140, filed Oct. 15, 2014.

BACKGROUND

Ruminants are mammals that are able to acquire nutrients from plant-based food by fermenting it in a specialized stomach prior to digestion, principally through bacterial actions. The process typically requires the fermented ingesta (known as cud) to be regurgitated and chewed again. The process of re-chewing the cud to further break down plant matter and stimulate digestion is called rumination. The rumen forms the larger part of the reticulorumen, which is the first chamber in the alimentary canal of ruminant animals. It serves as the primary site for microbial fermentation of ingested feed. There are about 150 species of ruminants, which include both domestic and wild species. Ruminating mammals include, but are not limited to: cattle, goats, sheep, giraffes, yaks, deer, camels, llamas, antelope, and some macropods.

Sub-acute ruminal acidosis (SARA), also known as chronic or sub-clinical acidosis, is a well-recognized digestive disorder that is an increasing health problem in most dairy herds. Results from field studies indicate a high prevalence of SARA in high-producing dairy herds as producers respond to the demands for increased milk production with higher grain, lower fiber diets that maximize energy intake during early lactation. Dairy herds experiencing SARA will have decreased efficiency of milk production, impaired cow health, and high rates of involuntary culling. The economic cost associated with SARA can be staggering. It is estimated that SARA costs the North American dairy industry between $500 million and $1 billion (USD) annually, with the costs per affected cow estimated at $1.12 (USD) per day. The challenge for dairy farmers and dairy nutritionists is to implement feeding management and husbandry practices that prevent or reduce the incidence of SARA, even in high-producing dairy herds to which higher levels of concentrate are fed to maximize energy intake.

Dietary buffers, such as sodium bicarbonate and sodium sesquicarbonate are commonly added to dairy rations to help manage SARA. Methods of feeding ruminants dietary buffers vary from mineral blocks to supplemented bunk fed total mixed rations (TMR). Research indicates that these buffers increase ruminal pH, and a feeding rate of 0.75% of ration dry matter (DM) is recommended. However, conventional dietary buffers are immediately solubilized in the rumen environment. Although conventional dietary buffers provide a degree of instant neutralization of rumen acid, they are unable to buffer post-meal rumen pH. Accordingly, there is a need in the industry to deliver dietary buffers to ruminants to provide a systematic, longer lasting buffer for acidic rumen conditions.

SUMMARY

Disclosed herein is a composition, comprising a mixture of discreet particles, each particle comprising an active substance and a coating material, the active substance being at least partially coated with the coating material. The mixture of discreet particles comprises a first batch of first particles, the first particles of the first batch having a first average weight % ratio of the active substance to the coating material; and a second batch of second particles, the second particles of the second batch having a second average weight % ratio of the active substance to the coating material, the second average weight ratio being different from the first average weight ratio.

Also disclosed is a method of making a composition that exhibits a multiphased, staggered, or sustained release of an active substance in a target environment, the method comprising obtaining a first batch of discreet first particles and obtaining a second batch of discreet second particles. In the first batch, each first particle comprises an active substance and a first coating material, the active substance being at least partially coated with the first coating material. In the second batch, each second particle comprises the active substance and a second coating material, the active substance being at least partially coated with the second coating material. The second coating material may be the same as the first coating material or different. The first batch of discreet first particles has a first release profile of the active substance in the target environment, and the second batch of discreet second particles has a second release profile of the active substance in the target environment that is different from the first release profile. The method further comprises mixing together the first batch of first particles with the second batch of second particles to obtain a mixture, wherein the mixture has a cumulative release profile of the active substance in the target environment that is different from the first release profile and the second release profile. Also disclosed are products comprising a composition obtained by this method.

Also disclosed is a method of buffering a rumen environment in a ruminant animal, the method comprising administering to the ruminant a rumen buffering composition. The rumen buffering composition comprises a mixture of discreet particles, each particle comprising a coating material and an active substance selected from the group consisting of alkali hydroxides, alkali metal oxides, alkali salts, sodium bicarbonate, potassium carbonate, potassium bicarbonate, magnesium carbonate, magnesium bicarbonate, calcium carbonate, calcium bicarbonate, sodium carbonate, sodium bicarbonate, sodium sesquicarbonate, ammonium carbonate, ammonium bicarbonate, and combinations thereof, the active substance being at least partially coated with the coating material. The mixture of discreet particles comprises a first batch of first particles, the first particles of the first batch having a first average weight % ratio of the active substance to the coating material; and a second batch of second particles, the second particles of the second batch having a second average weight % ratio of the active substance to the coating material, the second average weight ratio being different from the first average weight ratio.

BRIEF DESCRIPTION OF THE DRAWINGS

The embodiments and other features, advantages, and disclosures contained herein, and the manner of attaining them, will become apparent, and the present disclosure will be better understood by reference to the following description of various exemplary embodiments of the present disclosure taken in conjunction with the accompanying drawings, wherein.

DETAILED DESCRIPTION

Figure 1:
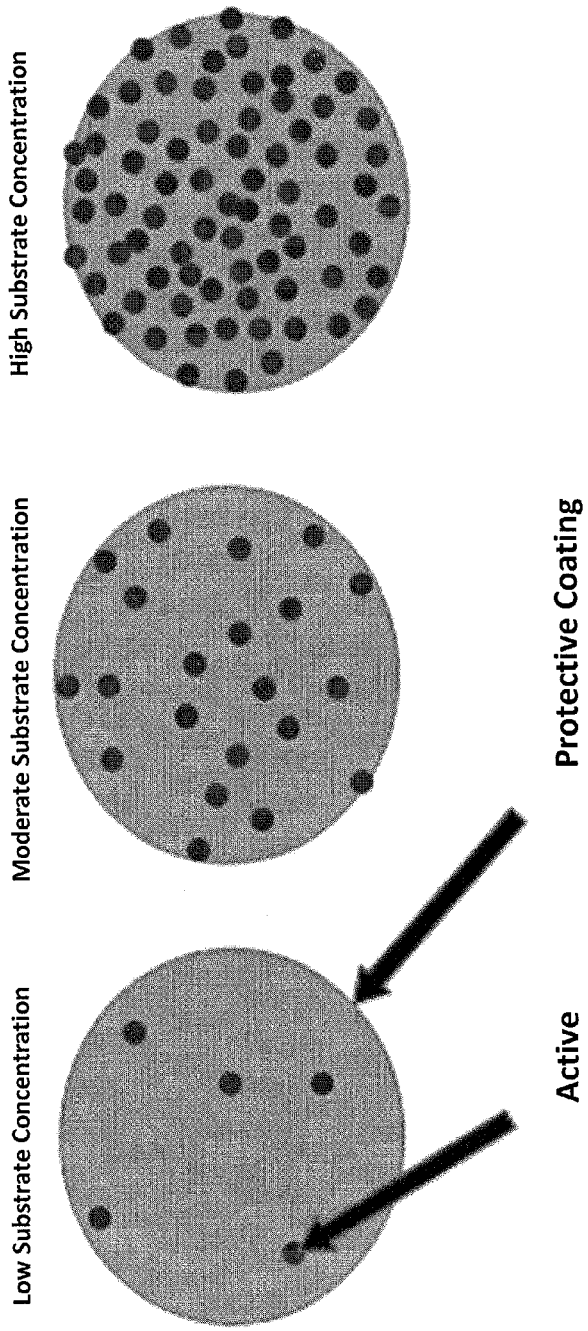
FIG. 1 is a schematic drawing of microencapsulating an active substance at three different concentrations into a matrix coating.

This disclosure is generally directed to compositions that are configured to provide a sustained release or a staggered/multiphase release of an active substance into a target environment. The compositions comprise a mixture of two or more different types of discreet particles comprising an active substance that is at least partially coated with a coating material. The particles of a given type of the discreet particles are substantially homogenous to each other in composition, shape, and size, and are thus substantially homogenous to each other with respect to the release profile of the active substance into the target environment. The release profile of an active substance includes the time delay, if any, from when the particle is exposed to the target environment and when the active substance begins to be released into the target environment from the particle. The release profile further includes the duration of release of the active substance from the particle into the target substance, as well as the rate of release of the active substance as a function of time. A mixture of two or more different types of the discreet particles, with each type having a different and distinct release profile from each other, may be used to achieve a sustained release or a staggered/multiphase release of the active substance into the target environment. The mixture may further contain discreet particles of non-coated active substance. As used herein, "conjugate release profile" refers to the release profile of the mixture.

The particles of coated active substance contain an active substance and a coating material. Some or all of the active substance in a particle may be partially coated or completely coated with the coating material. The active substance may be partially or completely encapsulated or microencapsulated by the coating material. The active substance may be contained in a single core that is coated with the coating material, or may be distributed in a matrix of the coating material, or may be contained in a central core and distributed in a matrix of the coating material coating the core. The active substance may be present in the particle as a solid, liquid, or a gas. In some embodiments, in a cross-section of the particle the active substance is indistinguishable from the coating material by a naked eye having 20/20 vision.

The particles may optionally further contain one or more excipients, such as binding substances, inert ingredients, and flow-control substances that together aid the formation of particles. A batch of particles and a mixture of different types of particles may contain one or more flow control substances.

The term "active substance" herein refers to any chemical element, compound, composition, or mixture that is the substance intended to be coated and released into the target environment to render an intended effect. The active substance may be selected from, for example, organic or inorganic acids and bases and their salts; buffer compositions; fertilizers; insecticides; acidulates; amino acids, enzymes, and proteins; nucleic acids; carbohydrates; probiotic microorganisms; prebiotic foods; vitamins; antibiotics; vermicides; antibodies; hormones; drugs; pharmaceuticals; perfumes; dyes; inks; adhesives; flavors; botanicals; essential oils; and natural extracts. These active substances may be used individually, or mixed together in varying weight ratios.

In some embodiments, the active substances include: alkali hydroxides, alkali metal oxides, alkali salts, sodium bicarbonate, potassium carbonate, potassium bicarbonate, magnesium carbonate, magnesium bicarbonate, calcium carbonate, calcium bicarbonate, sodium carbonate, sodium bicarbonate, sodium sesquicarbonate, ammonium carbonate, ammonium bicarbonate, and combinations thereof.

The coating material may comprise, consist of, or consist essentially of one or more selected from fatty acids, glycolipids, glycerolphopholipids, sphingolipids, sterol lipids, prenol lipids, saccharolipids, polyketides, monosaccharides, disaccharides, polysaccharides, ethyl cellulose, methyl cellulose, polyvinyl alcohol (PVA), gelatins, sodium alginate, agars, proteins, amino acids, and nucleic acids.

In some embodiments, the coating material comprises, consists of, or consists essentially of a vegetable oil, animal fat, a wax, or mixtures thereof. Suitable vegetable oils include palm oil, soybean oil, rapeseed oil, cottonseed oil, and castor oil. The vegetable oil may be partially or fully hydrogenated. Examples of suitable animal fats include tallow and lard. The animal fat may be partially or fully hydrogenated. Examples of waxes include carnauba wax, beeswax, paraffin wax, and other natural and synthetic waxes.

In some embodiments, the coating material has a melting temperature in the range of from about 40° C. to about 80° C., such as in the range of about 50° C. to about 60° C., or in the range of about 60° C. to about 70° C., or in the range of about 70° C. to about 80° C., or in the range of about 55° C. to about 65° C., or in the range of about 60° C. to about 75° C., to ensure that the coating on the final product has a hard surface, thereby preventing or reducing agglomeration of the final product during, for example, shipping or storage of the product.

The coating material may further comprise a modifying agent, such as, for example, stearic acid, oleic acid, lecithin, palm oil, and combinations thereof.

As used herein, "coating material" refers to everything present in a particle other than the active substance.

The release profile of a particle of a coated active substance depends on several different factors, including the ratio of active substance to the coating material, the shape of the particle, and the diameter of the particle. A number of other factors may affect the release profile, including the surface area of the outer surface of the particles, the presence of micropores and microfissures, the composition of the coating material, and the method of making the particles.

The release profile of a particle of a coated active substance is also dependent on the target environment. Typically, interaction between the target environment and the coating material affects the release of the active substance. For example, in the target environment, the coating material may dissolve by solvent action, melt due to temperature, or break down or weaken due to enzyme attack, chemical reaction, hydrolysis, slow disintegration, or biodegradation. Other mechanisms such as osmotic pressure and diffusion may factor in to the release profile. A given type of particle of a coated active substance may break down and release the active substance very quickly in one environment, while in another environment the particle may break down very slowly or not at all.

Two or more different types of particles, where each type of particle has a different release profile, may be mixed together to form a single composition. For example, first particles that each has a first release profile and second particle that each has a second release profile, wherein the first release profile is different from the second release profile, may be mixed together to obtain a mixture having a conjugate release profile that is different from the first and second release profiles. Or, the mixture could further contain third particles that each has a third release profile, the third release profile being different from the first, second, and conjugate release profiles. Or, the mixture could further contain any number of additional different types of such particles.

As used herein, a release profile is different from another release profile if at least one of the respective time delays of release, durations of release, or rates of release at a given time are different by at least: 1%, 2%, 3%, 4%, 5%, 6%, 7%, 8%, 9%, 10%, 11%, 12%, 13%, 14%, 15%, 16%, 17%, 18%, 19%, or 20%. The release profiles of different particles or of different batches of particles may be compared. The time delay of release is the amount of time, if any, from when the particle is exposed to the target environment and when the active substance begins to be released into the target environment from the particle. The duration of release of the active substance is the amount of time from when the active substance begins to be released into the target environment to when at least: 90%, 91%, 92%, 93%, 94%, 95%, 96%, 97%, 98%, 99%, or 100% of the active substance is released into the target environment. The rate of release of the active substance is the amount of active substance being released into the target environment as a function of time.

In some embodiments, different types of particles having different release profiles are obtained by producing different batches of particles, wherein the particles of different batches have a different ratio of the active substance to the coating material. The particles of a given batch have an average ratio of active substance (wt %) to coating material (wt %). The average ratio of the active substance to the coating material in a given batch may be anywhere from 0:100 to 100:0, Within a given batch, the ratio of active substance (wt %) to coating material (wt %) of the individual particles may independently vary from the average ratio. Preferably, at least 90% of the particles, by number of particles in the batch, have a ratio of active substance (wt %) to coating material (wt %) that is within 30% of the average ratio, such as within 20%, or within 15%, or 10%, or 5%, or 1%, or any other percentage between 30% and 1%, of the average ratio. The phrase "within X % of the average ratio" is intended to mean the range of A to B, inclusive of the end points A and B, where A=the average ratio−X % and B=the average ratio+X %.

A batch of particles having a given ratio of active substance (wt %) to coating material (wt %) may be produced by any suitable coating, encapsulation, or microencapsulation method known in the art. In some embodiments, such batches are produced by dispersing an amount of the active substance in molten coating material, wherein the ratio of weight of the active substance to the weight of the molten coating material is equal to the target ratio. The active material is preferably uniformly dispersed throughout the molten mixture. The molten mixture is then sprayed through a heated spray head into a chamber, and the droplets cool and solidify while falling through the chamber due to heat exchange between the molten material and cold air, forming solid microparticles.

Different batches of particles, where each batch has a different target ratio of active substance (wt %) to coating material (wt %) can be produced by adjusting the amount of active substance, or the amount of molten coating material, or both to obtain the target ratio. Particles from two or more different batches may be mixed together to form a single mixture of particles. The proportion by weight of the particles of a given batch of particles with respect to the total weight of particles in the mixture may be any value between 0% and 100%, excluding the end points. In some embodiments, the proportion by weight of each batch of particles comprising the mixture is substantially equal, such as within 5%, or 4%, or 3%, or 2%, or 1%, or 0.5%, or 0.1% of the total weight of particles divided by the number of batches of particles comprising the mixture. In some other embodiments, at least two batches, or three batches, or four batches, or five batches or more of particles each independently accounts for at least: 10%, or 9%, or 8%, or 7%, or 6%, or 5%, or 4%, or 3%, or 2%, or 1%, or 0.9%, or 0.8%, or 0.7%, or 0.6%, or 0.5%, or 0.4%, or 0.3%, or 0.2%, or 0.1% by weight of the total weight of particles in the mixture.

In some mixtures, after the particles from each batch are mixed together, it may be difficult to determine to which batch some of the particles belong, or how many batches of particles are represented in the mixture.

The $d_{50}$ of the particles, which is the particle diameter at which a cumulative percentage of 50% of the total particles are attained, may be in the range from about 8 μm to about 10,000 μm. In some embodiments, the $d_{50}$ of the final product may be in the range from about 8 μm to about 1000 μm, or from about 5000 μm to about 10,000 μm, or from about 200 μm to about 700 μm, or from about 400 μm to about 500 μm, or from about 1000 μm to about 5000 μm, or from about 600 μm to about 900 μm.

Methods for coating an active substance are known in the art, such as spray drying, spray chilling, spinning disk, fluid-bed coating, extrusion, co-extrusion, molecular encapsulation (such as cyclodextrins), spray drying and congealing using disks and nozzles, coacervation-phase separation, emulsion polymerization, liposomes, micelles, prilling, and others. Suitable methods will vary depending on the physical and chemical properties of the active substance, the coating material, the target environment, and the desired release profile. Suitable methods may include encapsulation and microencapsulation techniques.

One particular use of the inventive concepts disclosed herein is directed to a product that is configured to provide a systemic and sustained release of a buffering composition within the rumen of a ruminant Dietary buffers are commonly added to rations of dairy herds to help manage sub-acute ruminal acidosis (SARA), also known as chronic or sub-clinical acidosis SARA. Conventional dietary buffers are immediately solubilized in the rumen environment, providing a degree of instant neutralization of rumen acid. However, these conventional buffers do little to continue to buffer post-meal rumen pH. This problem is addressed by feeding the cows a buffer product comprising a mixture of two or more batches of particles of a coated buffer composition, where each batch of particles has a different average ratio of buffer composition (wt %) to coating material (wt %) in accordance with this disclosure.

Feeding to cows such a buffer product can provide a systematic and sustained release of the buffer composition to the rumen environment. Such a method may be used with any ruminant.

One of the direct benefits of a buffered rumen pH during feeding and the period of time following feeding is improved feed and forage uptake and improved digestion, including increased dry matter disappearance. These benefits, in turn, lead to improved live weight gain, and healthier herds with lower mortality rates, as well as higher milk yields, enhanced milk quality, and increased butterfat.

Increasing the dry matter disappearance increases milk production in ruminants. The more feed intake and greater feed efficiency that a ruminant has, the more milk it will produce. It is widely accepted that for every pound of gained feed efficiency, two pounds of milk are produced. See Amaral-Phillips et al., "More Feed=More Milk," University of Kentucky Cooperative Extension Service, pp. 1-5 (1997). Due to the increased dry matter disappearance and feed efficiency, a greater production of volatile fatty acids in the form of acetate, butyrate, and propionate occurs. These volatile fatty acids are the building blocks of milk proteins and muscle. As demonstrated in the Examples below, feeding cows mixtures of particles of coated buffer composition in accordance with this disclosure can increase the production of volatile fatty acids, and thus increase milk production in female ruminants.

Also, the buffer products discussed above may be configured to provide a source of fat supplements for cows and other ruminants For high producing herds, it has become a common practice to add fat to the diet of high producing dairy cows. Fat supplements provide a concentrated source of added energy without changing ration fiber and carbohydrate dynamics. The coating material of the buffer product can contain one or more of the lipids, fats, and oils discussed above or any other rumen-available fat or rumen-bypass fat known in the art.

EXAMPLES

Eight different formulations of encapsulated sodium bicarbonate ($NaHCO_3$) were produced. For each formulation, the coating material was a 50:50 blend (by weight) of hydrogenated soybean oil flakes (Cargill Stable Flake® S) and palm oil (Cargill TransAdvantage® P-130 NL NH). The coating ingredients (P-130 and Stable S) were melted at 175° F. Sodium bicarbonate ($NaHCO_3$) was then added to the melted coating ingredients, and the mixture was thoroughly mixed to obtain a substantially homogeneous mixture. The molten mixture was then sprayed through a heated spray head into a chamber, and the droplets cooled and solidified while falling through the chamber due to heat exchange between the molten material and cold air, forming solid lipid microparticles. The solid product was then gathered and screened with a #20 size screen.

Table 1 summarizes the ratio of the weight % of $NaHCO_3$ to the weight % of coating materials for these eight different formulations (Formulas A-H). A ninth formulation, Formula I, was uncoated $NaHCO_3$.

TABLE 1

Ratios of $NaHCO_3$ to Coating Material

| Formula | $NaHCO_3$ (wt %) | Coating Material (wt %) |
|---|---|---|
| A | 10 | 90 |
| B | 12.5 | 87.5 |
| C | 15 | 85 |
| D | 20 | 80 |
| E | 30 | 70 |
| F | 40 | 60 |
| G | 50 | 50 |
| H | 60 | 40 |
| I | 100 | 0 |

Figure 12:
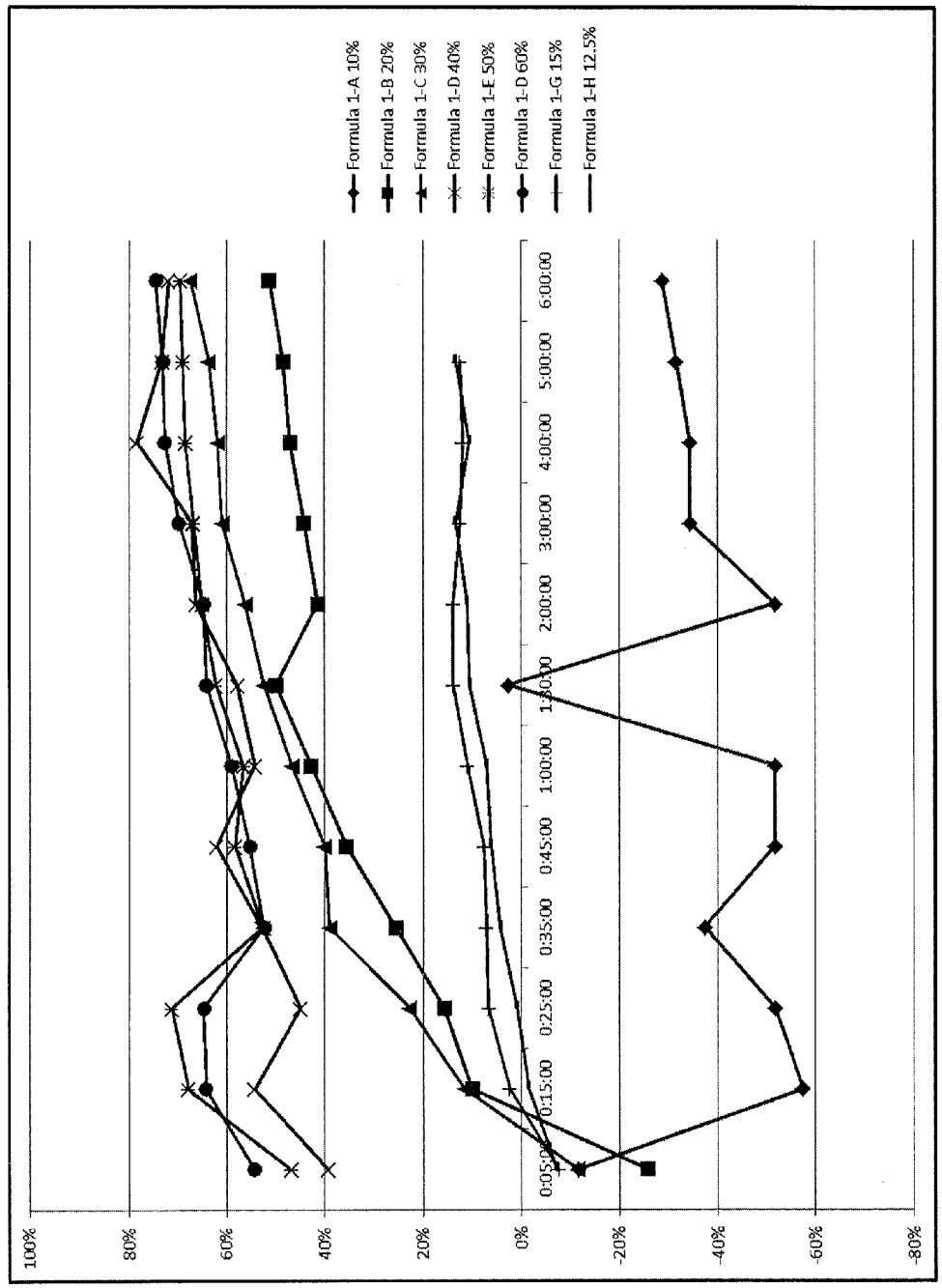
FIG. 12 shows a line graph illustrating that matrix spheres containing lower amounts of sodium bicarbonate buffer will go into solution at a much slower rate. Conversely, high substrate concentrations will go into solution at a faster rate.

Capsules containing lower $NaHCO_3$ content (e.g., Formula A 10%) will have a much thicker shell wall than capsules containing higher $NaHCO_3$ content (i.e., Stage 1 Formula 1-F 60%). Internal solubility tests showed capsules with larger shells are less soluble than capsules than capsule with thin shells. See FIG. 12.

Example 1

In Vitro Testing

Three separate products, each being a mixture of particle of five different Formulas of Table 1, were obtained. Also prepared was a fourth product, consisting entirely of non-encapsulated sodium bicarbonate ("Control"). The compositions of these products are summarized in Table 2.

TABLE 2

Different Product Formulations

| Product | Formula With Ratio Of $NaHCO_3$ To Coating Material | Wt % Of Formula With Respect To Total Weight Of Product |
|---|---|---|
| 1 | J (100:0) | 20 |
|   | H (60:40) | 20 |
|   | E (30:70) | 20 |
|   | D (20:80) | 20 |
|   | A (10:90) | 20 |
| 2 | H (60:40) | 20 |
|   | E (30:70) | 20 |
|   | D (20:80) | 20 |
|   | C (15:85) | 20 |
|   | A (10:90) | 20 |
| 3 | E (30:70) | 20 |
|   | D (20:80) | 20 |
|   | C (15:85) | 20 |
|   | B (12.5:87.5) | 20 |
|   | A (10:90) | 20 |
| CONTROL | J (100:0) | 100 |

Each of the products was tested using in vitro ruminal incubation to determine the product's influence on ruminal pH, volatile fatty acid production in relation to changes in ruminal pH, and the associative effects of ruminal pH and volatile fatty acid on dry matter disappearance, starch disappearance, and neutral detergent fiber disappearance.

Incubation solution containing water, composited rumen contents, and Van Soest buffer was placed in 1 L-incubation vessels (1 L oval deli cup with lid and Bunsen valve). Simulated feeding bags were obtained by placing 3 g of ground (Wiley Mill, 8 mm screen) total meal rations (10% alfalfa hay, 35% corn silage, 50% corn grain, and 5% vitamin/minerals) into 5 cm×10 cm bags with a pore size of 40 microns. Product 1 was added to each of eight replicate feeding bags in an amount at 0.2273 g/L. Product 2 was added to another set of eight replicate bags in an amount of 0.3704 g/L. Product 3 was added to another set of eight replicate bags in an amount of 0.5710 g/L. Control was added to another set of eight replicate bags in an amount of 0.1 g/L. A fifth set of eight replicate bags contained just the 3g of ground total meal rations to serve as a "Blank" control.

To simulate twice-a-day-feeding, four replicates from each set of replicates were added to the incubation vessels at zero hours (0 H), and four more were added at twelve hours (12 H). The incubation vessels were placed into a temperature controlled, air jacketed, anaerobic incubator (39° C., and 20% carbon dioxide) for the duration of their assigned incubation time.

Ruminal pH was measured during each incubation time. At zero hours and twelve hours, pH was also recorded before and after the simulated feeding. Volatile fatty acid production was measured by taking 50 ml aliquots of the supernatant of each incubation vessel at 0, 2, 6, 12, 14, 18, and 24 hours, acidifying the aliquot with 5 ml of 50% HCl, and freezing it for future analysis. Dry matter disappearance, starch disappearance, and neutral detergent fiber disappearance were measured by removing replicate bags at the same hours the volatile fatty acid aliquots were taken, drying them in a forced-air oven at 60° C. to a constant weight, and storing them for future analysis.

Changes in pH

Figure 2:
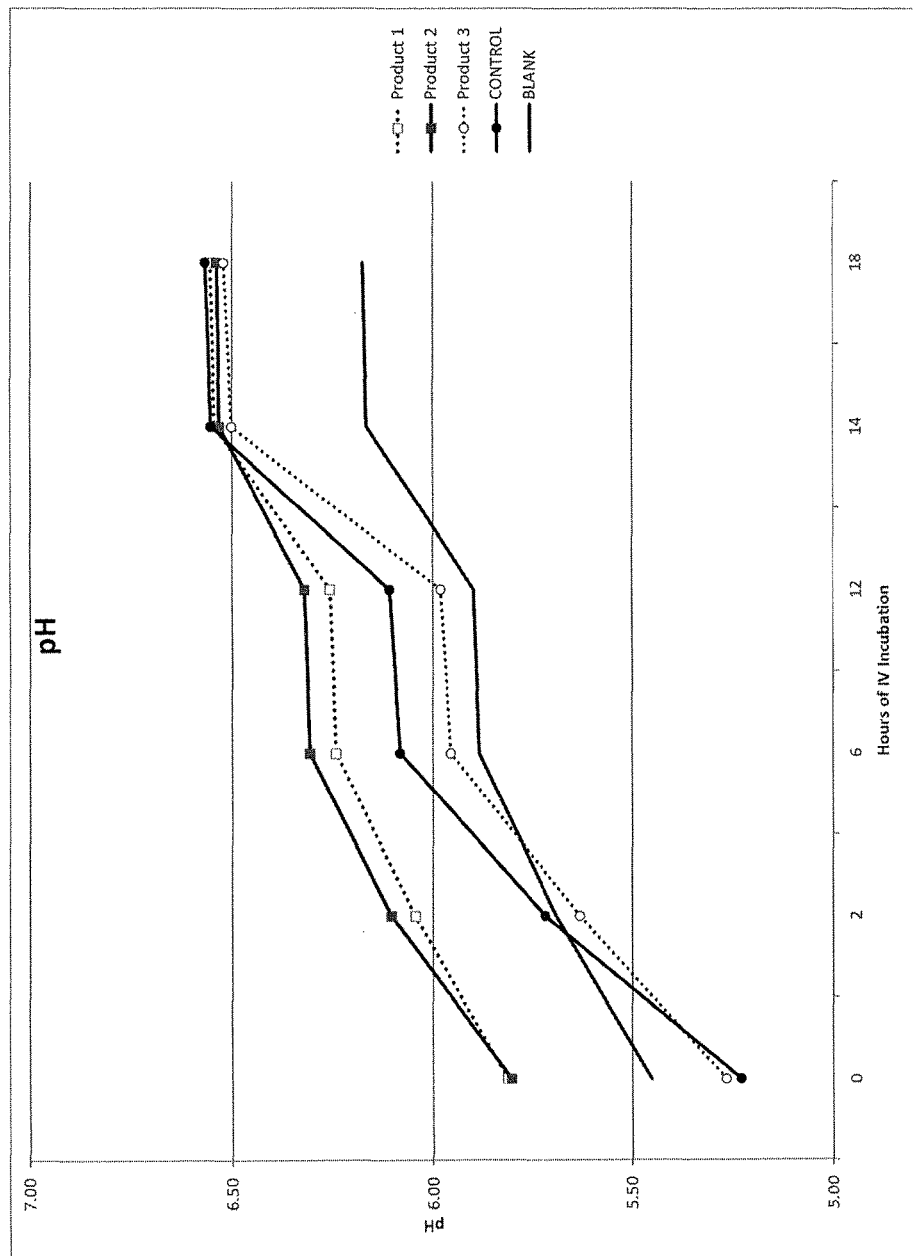
FIG. 2 shows a line graph illustrating changes in pH during 36 hours of in vitro incubation for Products 1, 2, and 3, Control, and Blank.
Figure 3:
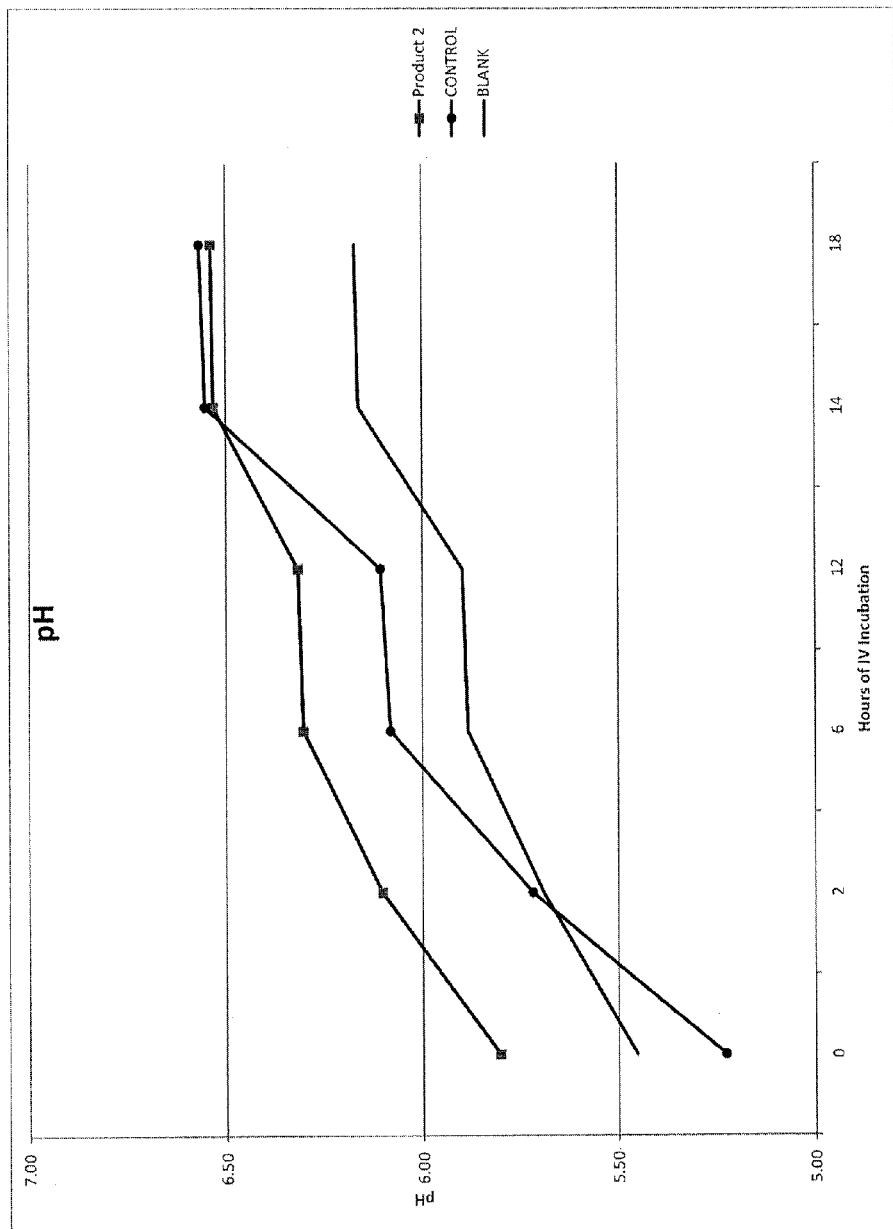
FIG. 3 shows a line graph illustrating changes in pH during 36 hours of in vitro incubation for Product 2.

In FIG. 2, the pH measurements showed a starting pH at 0 H with a gradual decline until the next feeding at 12 H. FIG. 3 shows the curve for Product 2, High pH is associated with higher total volatile fatty acids and acetic acid, which demonstrates the buffering effect of the product.

Changes in Volatile Fatty Acids

Figure 4:
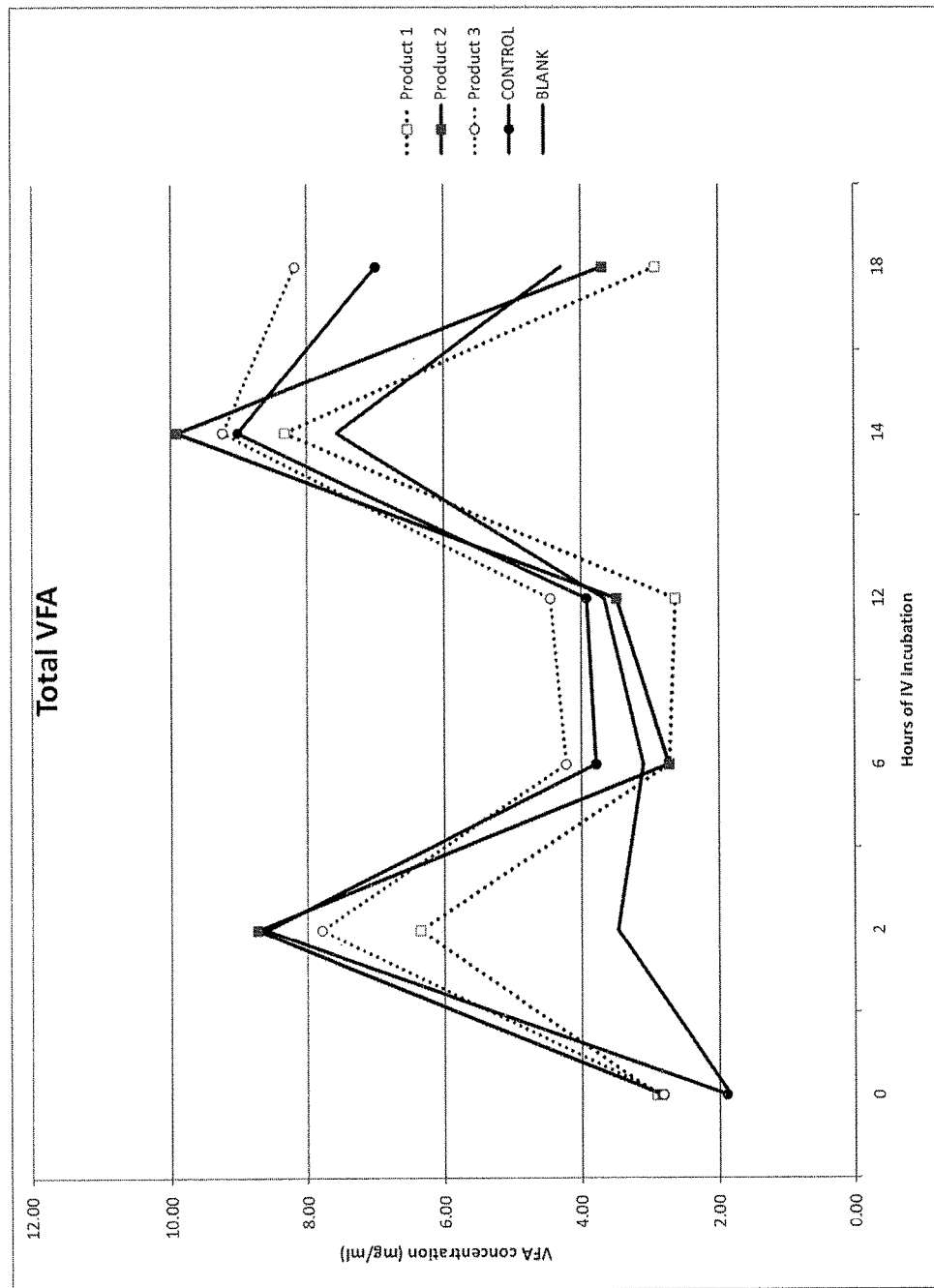
FIG. 4 shows a line graph illustrating changes in total volatile fatty acid (VFA) concentration during 18 hours of in vitro incubation for Products 1, 2, and 3, Control, and Blank.

As shown in FIG. 4, volatile fatty acids concentrations were measured at the following hours of incubation: 0, 2, 6, 12, 14 and 18, At time 0 H, the baseline concentration was established for the rumen fluid solution. The first feeding was monitored for 12 hours (2, 6, and 12). Then the second feeding was monitored at 14 and 18 hours which corresponded to the 2 and 6 hours post-feeding. The rumen fluid was more active at the second than at the first feeding.

Product 2 was similar to Control in production of total volatile fatty acids in the period of 0 to 12 hours. Its curve during this period is masked by the curve for Control. However, these two curves are more distinguishable after the second feeding (12 H), with Control showing a higher concentration at 18 H compared to that of Product 2, Product 1 and Blank also show a decline in total volatile fatty acids after 2 hours, with Product 1 having the lowest total volatile fatty acids production compared to the other products.

Figure 5:
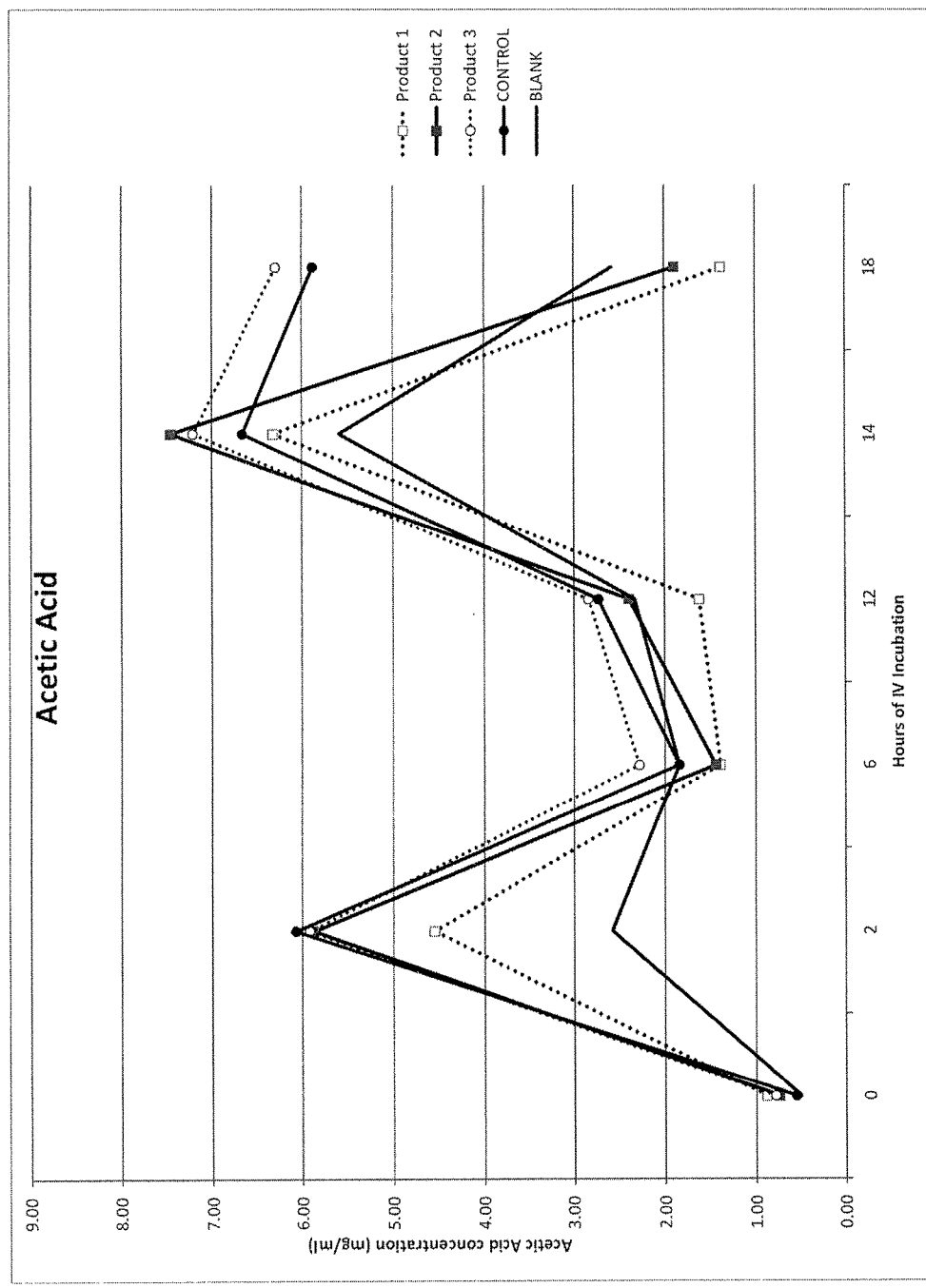
FIG. 5 shows a line graph illustrating changes in acetic acid concentration during 18 hours of in vitro incubation for Products 1, 2, and 3, Control, and Blank.
Figure 6:
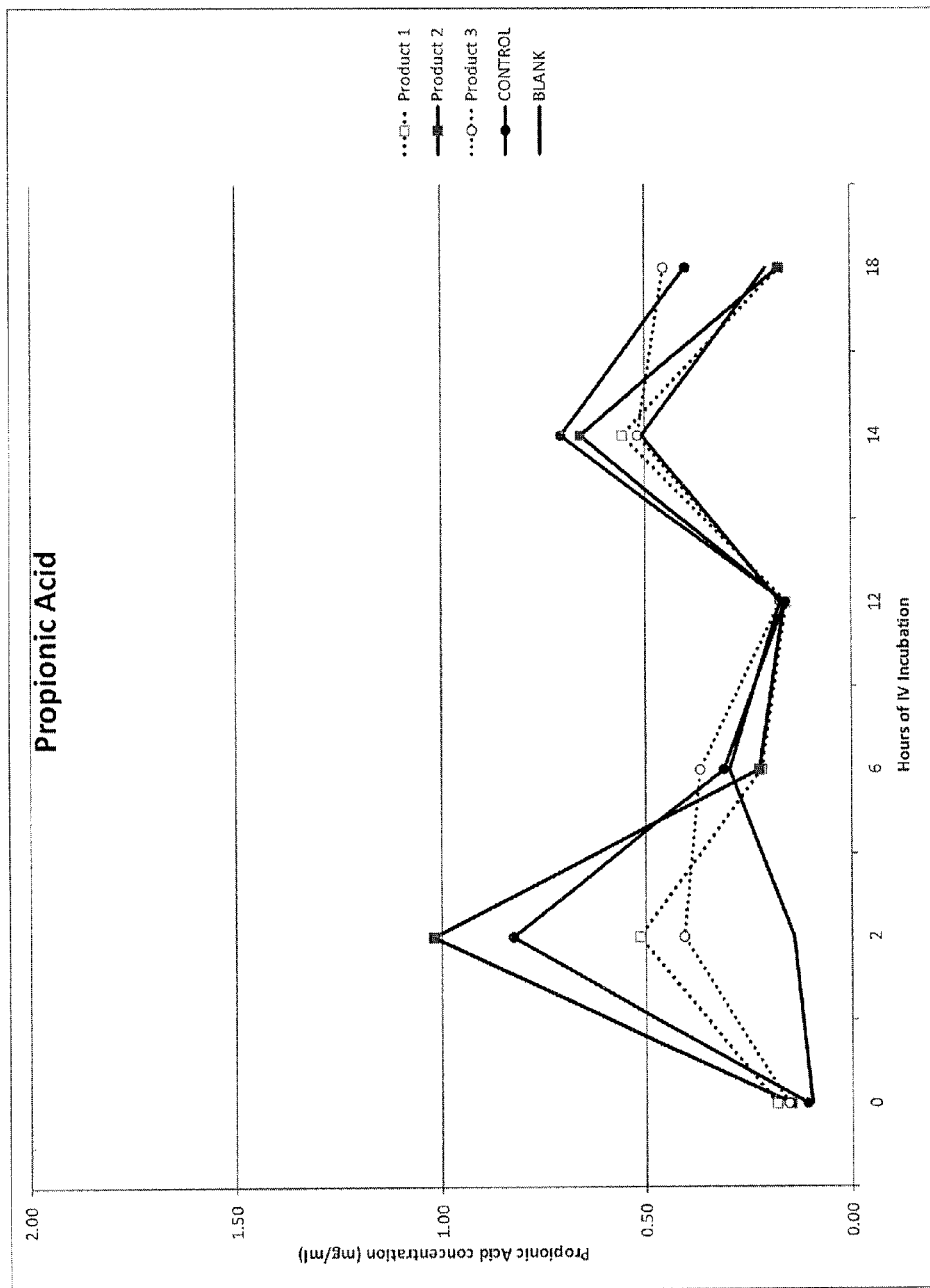
FIG. 6 shows a line graph illustrating changes in propionic acid concentration during 18 hours of in vitro incubation for Products 1, 2, and 3, Control, and Blank.
Figure 7:
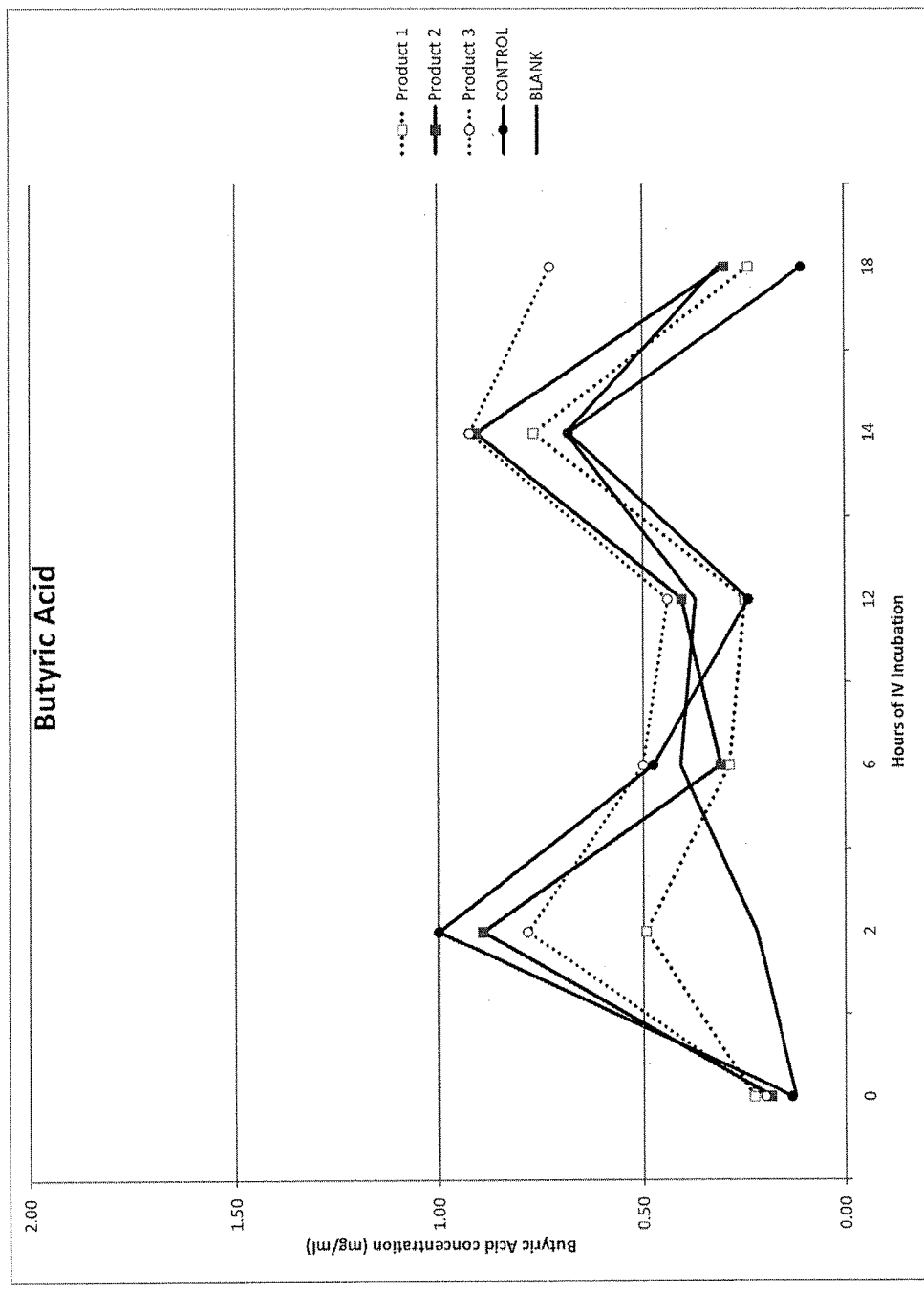
FIG. 7 shows a line graph illustrating changes in butyric acid concentration during 18 hours of in vitro incubation for Products 1, 2, and 3, Control, and Blank.

FIGS. 5-7 show that the major contributor to total volatile fatty acids concentrations is acetic acid for all of the products. Data gleaned from these figures also show that there are differences between each product with respect to (1) the acetic acid to propionic acid ratios (A:P), and (2) the sum of acetic acid and butyric acid to propionic acid ratios (AB:P). These ratios are summarized in Table 3 for the overall values at 18 hours, and at the two peaks of 2 and 14 hours.

TABLE 3

Ratios Of Even To Odd Chained VFAs During In vitro Incubation

| Product | 18 Hours | | At Peak Concentrations | |
|---|---|---|---|---|
| | A:P | AB:P | A:P Peaks | AB:P Peaks |
| 1 | 11.00 | 12.05 | 10.15 | 11.32 |
| 2 | 10.19 | 11.24 | 7.93 | 9.00 |
| 3 | 15.02 | 16.46 | 14.18 | 16.02 |
| CONTROL | 11.61 | 12.50 | 8.30 | 9.39 |
| BLANK | 13.31 | 14.57 | 12.57 | 13.97 |

Acetic acid and butyric acid each has an even numbers of carbons in its chain length (2 and 4, respectively) and can be sources of milk fat. Propionic acid has 3 carbons and is quickly assimilated into energy production via microbial utilization of the Embden-Myerhof pathway. Because microbial function and milk production each requires a source of raw materials and energy for their synthetic pathways, a ratio of even-numbered carbon chains to odd-numbered carbon chains allows for efficient synthesis. As seen from Table 3, Product 2 appears to be slightly superior to Control, and both Product 2 and Control appear to be superior to the other treatments. This superiority is shown by a relatively high amount of total volatile fatty acids, plus a high amount of propionic acid without an associated decrease in the amount of acetic acid. For all the products, the concentration of butyric acid is not indicative of an abnormal fermentation.

Figure 8:
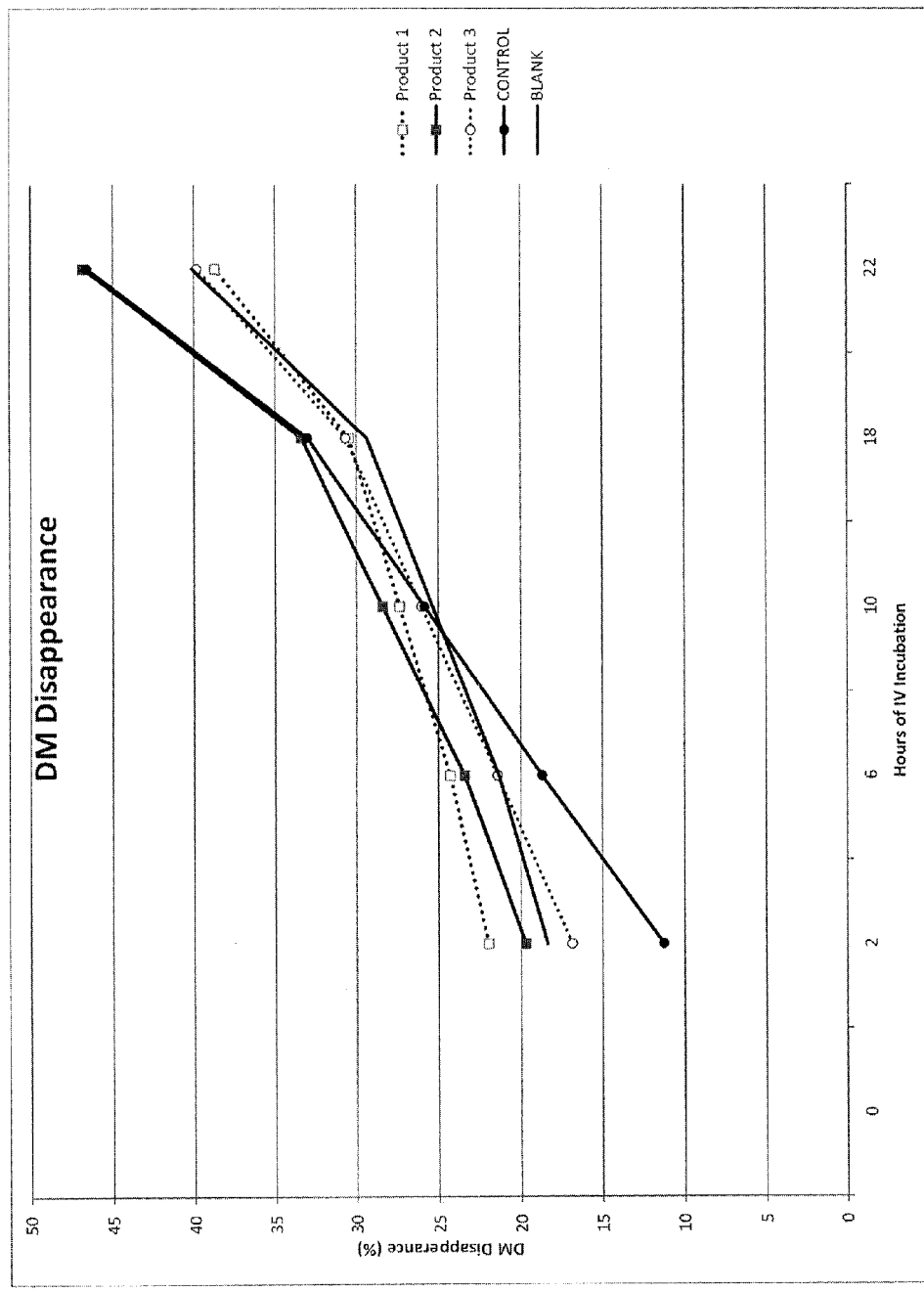
FIG. 8 shows a line graph illustrating changes in dry matter (DM) disappearance (DMD) during in vitro incubations for Products 1, 2, and 3, Control, and Blank.
Figure 9:
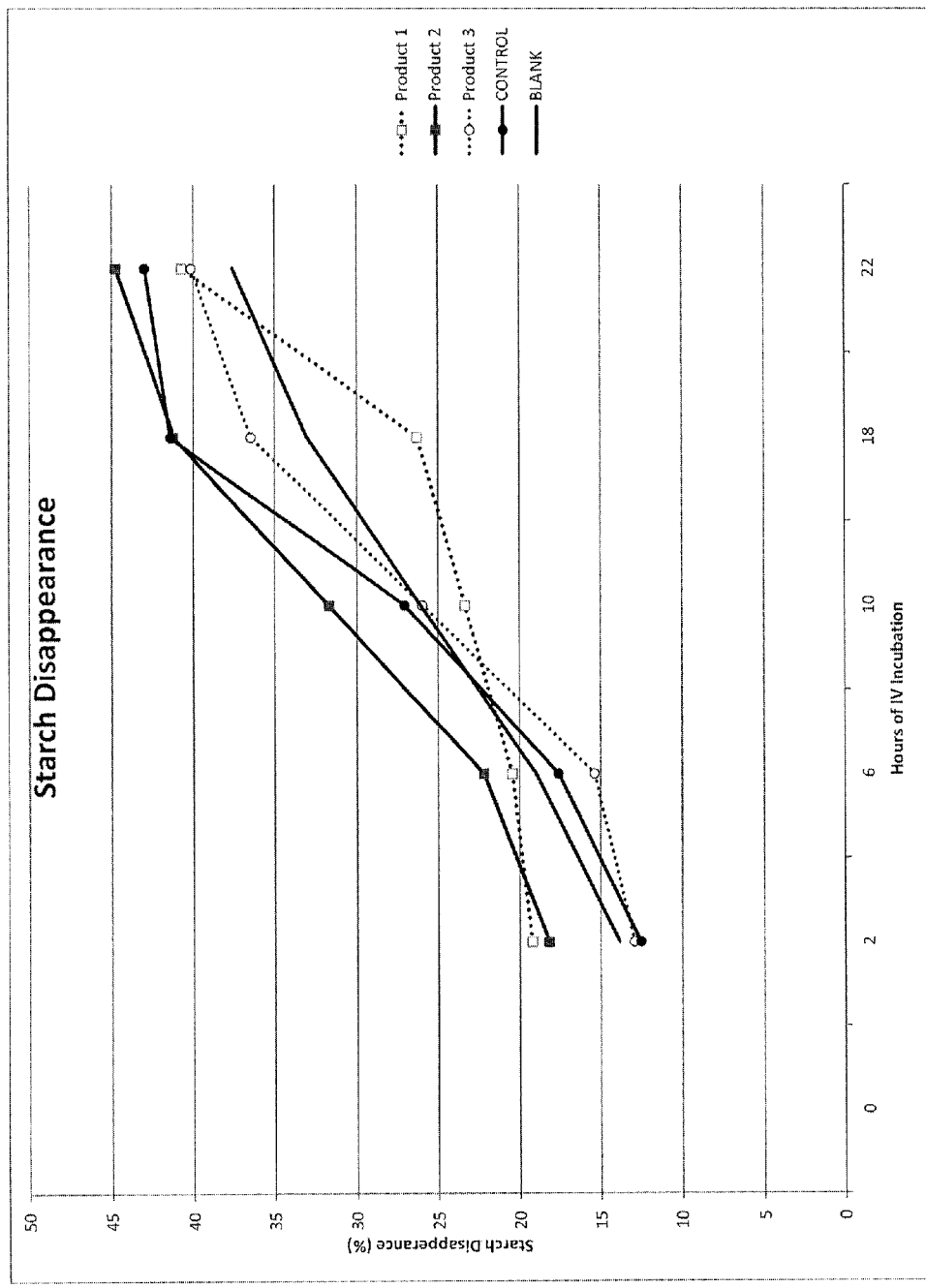
FIG. 9 shows a line graph illustrating changes in starch (STR) disappearance (STRD) during in vitro incubations for Products 1, 2, and 3, Control, and Blank.
Figure 10:
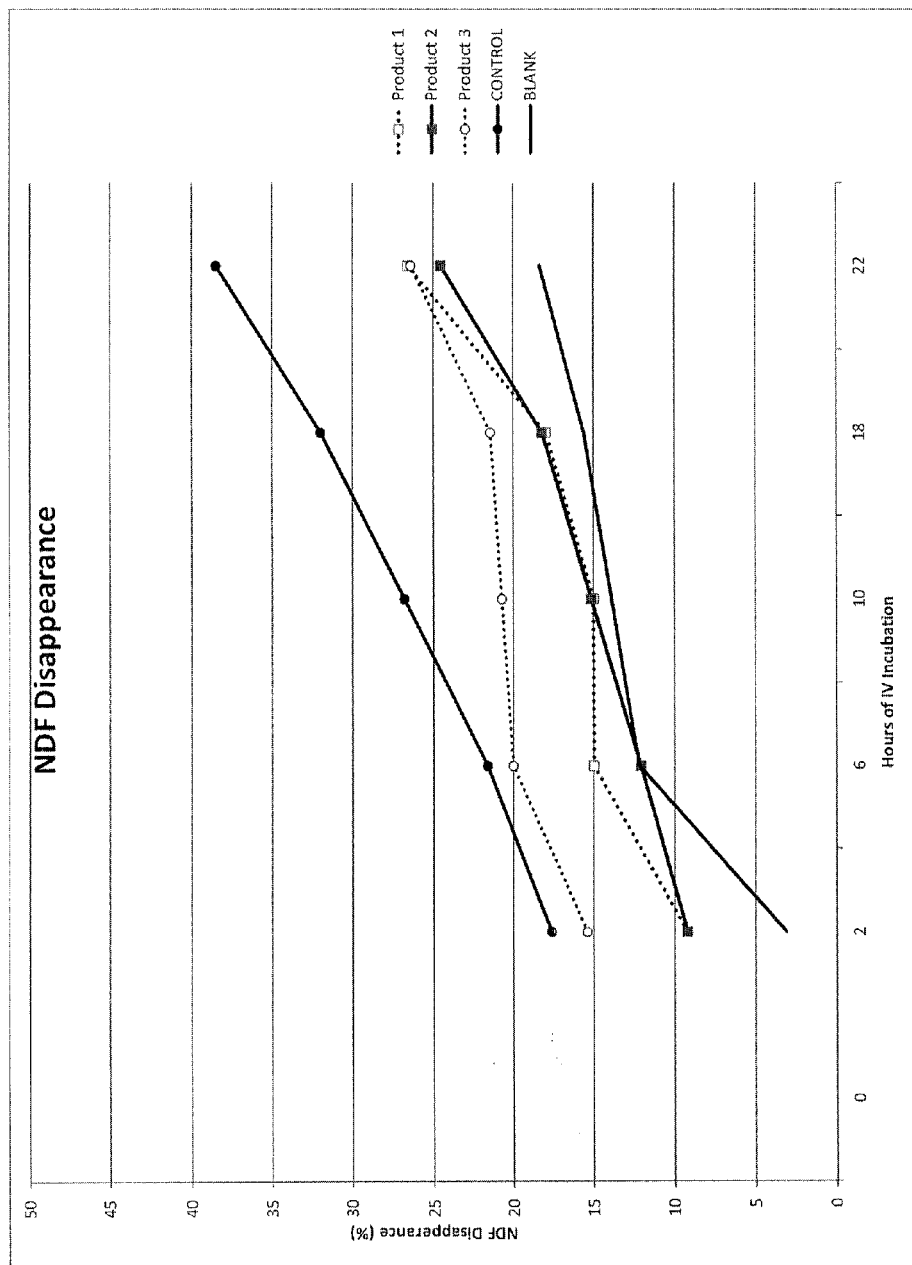
FIG. 10 shows a line graph illustrating changes in neutral detergent fiber (NDF) disappearance (NDFD) during in vitro incubations for Products 1, 2, and 3, Control, and Blank.

Changes in dry matter disappearance, starch disappearance, and neutral detergent fiber disappearance Dry matter, starch, and neutral detergent fiber concentrations were measured at 2, 4, 6, 10, 12, 16, 18, and 22 hours of incubation. The measurements for starch disappearance and neutral detergent fiber disappearance were made at 2, 6, 16, and 22 hours of incubation. The early times were selected to monitor the faster degradation of starch, and the later times to monitor the slower degradation of neutral detergent fiber. FIGS. 8-10 respectively show the disappearance curves for dry matter disappearance, starch disappearance, and neutral detergent fiber disappearance.

Ration dry matter is the raw material for microbial fermentation within the rumen and is the substrate from which volatile fatty acids and microbial biomass arise. FIGS. 8 and 9 show Product 2 and Control obtained the best results for dry matter disappearance and starch disappearance. This is most likely the source of their superior production of propionic acid (FIG. 6).

In FIG. 10, Control demonstrated higher neutral detergent fiber disappearance over Products 1, 2, and 3, and Blank. However, it is known that feeding fat supplements to cows can absorb on bacteria in the rumen, thus lowering the bacteria's ability to breakdown the feed, and coat the feed particles, making the feed particles more difficult to digest in the rumen. In these Examples, there were no fats present in the Control, while fat was a substantial component of Products 1, 2, and 3, Despite this fact, dry matter disappearance and starch disappearance were the highest with Product 2, Because dry matter disappearance is the result of both neutral detergent fiber and starch disappearance, the fact that dry matter disappearance and starch disappearance are the highest with Product 2 appears to indicate that the lowering of neutral detergent fiber disappearance of Product 2 over Control was not a large, negative influence on the total dry matter disappearance of Product 2, Overall, Product 2 influences ruminal pH, and this influence affects volatile fatty acids production plus dry matter disappearance, neutral detergent fiber disappearance, and starch disappearance.

Figure 11:
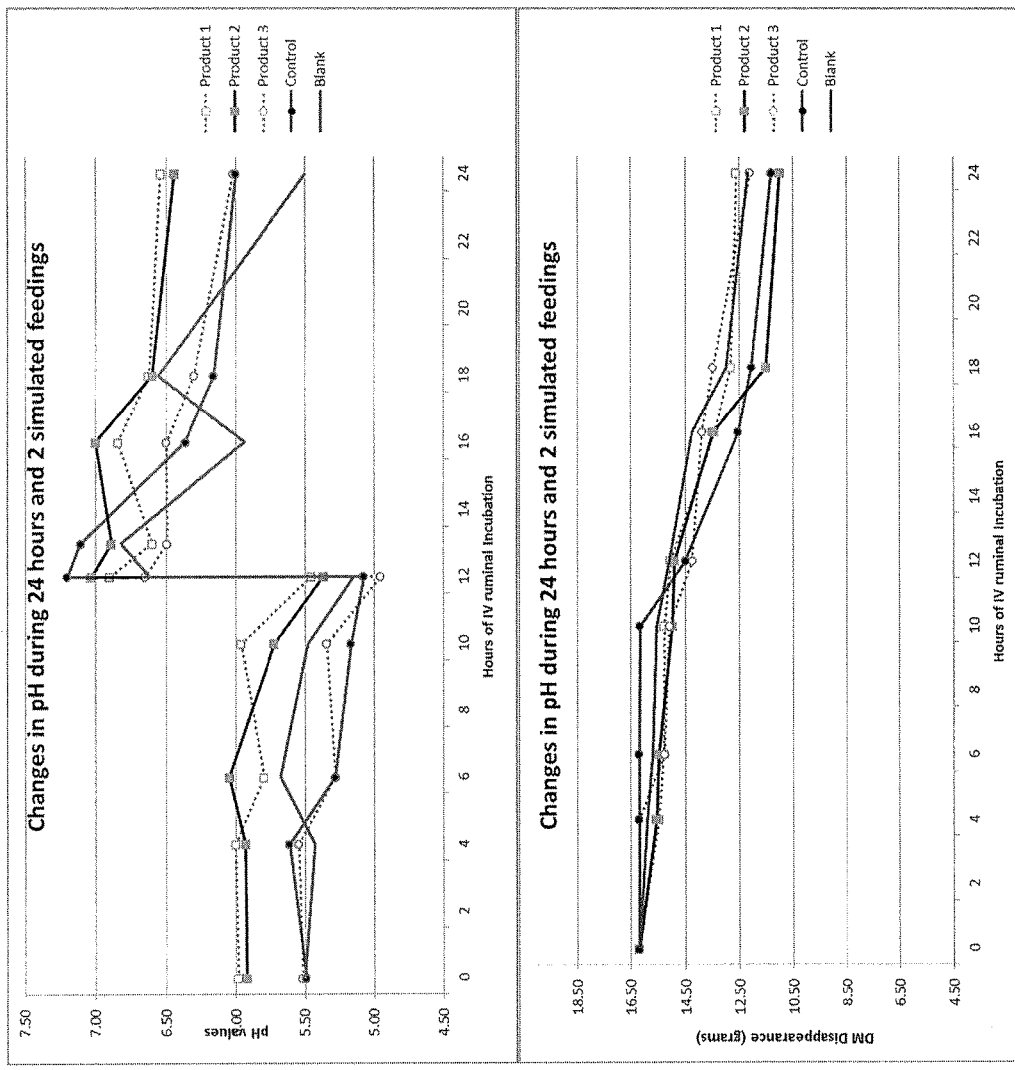
FIG. 11 shows a line graph illustrating changes in DMD and pH during 24 hours of in vitro incubation and two in vitro simulated ruminal feedings.

FIG. 11 shows the changes in pH and the changes in dry matter disappearance during 24 hours for the two simulated feedings. Ruminal pH is generally highest over the course of the 24-hour incubation period with Product 2, With regard to pH changes, Products 1 and 2 are clearly superior to Product 3, Control, and Blank in maintaining a higher pH, especially at the onset of ruminal fermentation.

Over a 24 hour feeding cycle, Product 2 consistently provided a sustained buffering of rumen pH that was moderately and intentionally raised from the sub-acute acidotic state. Feeding of Control offered only a "flash" neutralization that was soon dissipated. It was also discovered that Control showed little dry matter disappearance in the first 11 hours of the feeding cycle, which is very inefficient. As already pointed out, Product 2 showed a significant increase of dry matter disappearance over the Control.

While embodiments of the disclosed compositions and methods employing the same have been described herein, the embodiments are merely offered by way of non-limiting examples of the disclosure described herein. It will therefore be understood that various changes and modifications may be made, and equivalents may be substituted for elements thereof, without departing from the scope of the disclosure and are intended to encompass any later appended claims. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

What is claimed:

1. A composition, comprising:
   a mixture of discreet particles, each particle comprising:
   an active substance; and
   a coating material;
   the active substance being at least partially coated with the coating material;
   the mixture of discreet particles comprising:
   a first batch of first particles, the first particles of the first batch having a first average weight % ratio of the active substance to the coating material; and
   a second batch of second particles, the second particles of the second batch having a second average weight % ratio of the active substance to the coating material, the second average weight ratio being different from the first average weight ratio by at least 0.03.

2. The composition of claim 1, wherein the active substance comprises at least one selected from the group consisting of: organic or inorganic acids and bases and their salts; buffer compositions; fertilizers; insecticides; acidulates; amino acids, enzymes, and proteins; nucleic acids; carbohydrates; probiotic micro-organisms; prebiotic foods; vitamins; antibiotics; vermicides; antibodies; hormones; drugs; pharmaceuticals; perfumes; dyes; inks; adhesives; flavors; botanicals; essential oils; and natural extracts.

3. The composition of claim 1, wherein the coating material comprises at least one selected from the group consisting of:
   fatty acids, glycolipids, glycerolphopholipids, sphingolipids, sterol lipids, prenol lipids, saccharolipids, polyketides, monosaccharides, disaccharides, polysaccharides, ethyl cellulose, methyl cellulose, polyvinyl alcohol (PVA), gelatins, sodium alginate, agars, proteins, amino acids, and nucleic acids.

4. The composition of claim 1, wherein in each particle the active substance is contained in a single core, and the core is at least partially coated with the coating material.

5. The composition of claim 1, wherein in each particle the active substance is contained in two or more granules, and the granules are at least partially coated with the coating material.

6. The composition of claim 1, wherein each particle comprises a mixture of the active substance in a matrix of coating material, and in a cross-section of the particle the active substance is indistinguishable from the coating material.

7. The composition of claim 1, wherein an amount of first particles in the mixture of discreet particles is at least 1 wt % of a total weight of the mixture of discreet particles.

8. The composition of claim 1, wherein an amount of second particles in the mixture of discreet particles is at least 1 wt % of a total weight of the mixture of discreet particles.

9. The composition of claim 1, wherein the mixture of discreet particles further comprises:
   a third batch of third particles, the third particles of the third batch having a third average weight % ratio of the active substance to the coating material, the third average weight ratio being different from the first average weight ratio and the second average weight ratio by at least 0.03.

10. The composition of claim 1, wherein the first particles have an average diameter of about 8 μm to about 1000 μm.

11. The composition of claim 1, wherein:
    the active substance is selected from the group consisting of alkali hydroxides, alkali metal oxides, alkali salts, sodium bicarbonate, potassium carbonate, potassium bicarbonate, magnesium carbonate, magnesium bicarbonate, calcium carbonate, calcium bicarbonate, sodium carbonate, sodium bicarbonate, sodium sesquicarbonate, ammonium carbonate, ammonium bicarbonate, and combinations thereof; and
    the coating material comprises a lipid composition selected from the group consisting of a vegetable oil, animal fat, a wax, or mixtures thereof.

* * * * *